United States Patent [19]

Uwaydah et al.

[11] Patent Number: 5,696,274
[45] Date of Patent: Dec. 9, 1997

[54] SYNTHESES BASED ON 2-HYDROXYACETOPHENONE

[75] Inventors: Ibrahim M. Uwaydah; Mohammad Aslam, both of Corpus Christi, Tex.; Charles H. Brown, II, North Kingstown, R.I.; Sharon R. Fitzhenry, Foxboro, Mass.; Joseph A. McDonough, West Greenwich, R.I.

[73] Assignee: Hoechst Celanese Corporation, Somerville, N.J.

[21] Appl. No.: 651,599

[22] Filed: May 22, 1996

Related U.S. Application Data

[60] Provisional application No. 60/009,416, Dec. 28, 1995.
[51] Int. Cl.⁶ .................................................. C07D 311/02
[52] U.S. Cl. .................................. 549/285; 549/286
[58] Field of Search ................................ 549/285, 286

[56] References Cited

U.S. PATENT DOCUMENTS

| | | | |
|---|---|---|---|
| 2,752,360 | 6/1956 | Starr et al. | 260/343.2 |
| 2,765,321 | 10/1956 | Schroeder et al. | 260/343.2 |
| 2,777,859 | 1/1957 | Link | 260/343.2 |
| 3,077,481 | 2/1963 | Schroeder et al. | 260/343.2 |
| 3,246,013 | 4/1966 | Weiner et al. | 260/343.2 |
| 4,113,744 | 9/1978 | Badran | 260/343.44 |
| 4,826,689 | 5/1989 | Violanto et al. | 424/489 |

OTHER PUBLICATIONS

Rodney C. Hayward, Journal of Chemical Education, vol. 61, No. 1, 87 (1984).

*Primary Examiner*—Amelia Owens
*Attorney, Agent, or Firm*—M. Susan Spiering; Jerome Rosenstock; Michael W. Ferrell

[57] ABSTRACT

The present invention provides processes which are flexible, cost effective, and commercially viable methods of manufacturing or producing products from 2-hydroxyacetophenone (2-HAP).

Of particular interest of the available products are 4-hydroxycoumarin, warfarin-alkali salt, preferably warfarin sodium and warfarin-alkali salt-isopropyl alcohol (2-propanol) complex, more preferably warfarin-sodium-isopropyl alcohol complex.

As is known, these compounds are useful as vitamin K dependent anticoagulants in the treatment of humans and animals. In different doses, they are also useful as rodenticide.

The inventive process involves contacting 2-HAP, carbonate ester and effective base followed by treatment with an unsaturated ketone and phase transfer catalyst to ultimately yield product.

18 Claims, No Drawings

SYNTHESES BASED ON 2-HYDROXYACETOPHENONE

This is a NON-PROVISIONAL PATENT APPLICATION, said application claiming the benefit under 35 U.S.C. §119(e) of a Provisional Patent Application, Application Number 60/009,416, filed on Dec. 28, 1995, and said APPLICATION being executed as a Non-Provisional application for filing under 35 USC 111(a) and 1.53(b)(1) concurrently herewith.

FIELD OF THE INVENTION

This invention relates to compounds which may be synthesized from 2-Hydroxyacetophenone in commercially feasible and cost-effective fashion.

BACKGROUND OF THE INVENTION

In the commercial production of various organic compounds it is useful to have flexible systems which can be tailored to production needs at any given time. In production of pharmaceutical materials it is highly desirable to have systems and production protocols which provide clean manufacturing and do not provide multiple transfers and cleaning steps during which contaminants may be introduced. As the background demonstrates numerous others have provided means or syntheses, usually including multiple steps, for reaching a single compound at a single endpoint.

Starr et al. describe, in U.S. Pat. No. 2,752,360, improvement in the manufacture of 3-substituted 4-hydroxycoumarins by heating the ethyl ester of 3-carboxy-4-hydroxycoumarin with an α,β-unsaturated ketone selected from: benzalacetone, benzalacetophenone, anisal acetone, and parachlorbenzalacetone, dispersed in water in the presence of ammonia, lower tertiary alkyl amines, aniline, or pyridine.

Schroeder et al. describe, in U.S. Pat. No. 2,765,321, a process of preparing crystalline, stable, free-flowing warfarin sodium from aqueous solutions of warfarin sodium by reacting aqueous sodium hydroxide with excess warfarin and removing the excess warfarin through the addition of ethanol to the warfarin sodium solution, lithium chloride to the aqueous-ethanol solution, cooling while stirring, and finally recovering the resulting warfarin sodium crystals.

Link et al. describe, in U.S. Pat. No. 2,777,859, a process of preparing an aqueous solution of warfarin-alkali metal derivative by slowly adding aqueous alkali metal hydroxide, with stirring, with an excess of water wet warfarin, warming, and removing the excess warfarin from the solution.

Schroeder et al. describe, in U.S. Pat. No. 3,077,481, a process of purifying warfarin sodium by dissolving amorphous warfarin sodium in warm isopropyl alcohol, cooling, and recovering the crystalline product.

Weiner et al. describe, in U.S. Pat. No. 3,246,013, a process for preparing the crystalline warfarin sodium-isopropyl alcohol complex through neutralization, to a pH of about 9–10, of warfarin in a warfarin-isopropyl alcohol slurry with sodium hydroxide or selected sodium alkyl oxides at about 50°–80° C.

Badran describes, in U.S. Pat. No. 4,113,744, a method for production of warfarin acid crystals within a specified length range by dissolving warfarin in an aqueous buffered solution, using any of several designated buffers or their combinations, with a pH of 7–10. The pH of the solution is then brought to 8.0–9.0, impurities are then removed by filtration or centrifugation, followed by buffer neutralization to a pH of 5.0–7.0, and recovering precipitated microcrystalline warfarin.

Violanto et al. describe, in U.S. Pat. No. 4,826,689, a method of making uniformly sized particles of a solid, water-insoluble organic compound by preparing a solution of the solid organic compound in a water-miscible organic solvent and infusing an aqueous precipitating liquid into the organic solution at a temperature between about –10° C. and about 100° C. at a specified slow rate of infusion to produce a suspension of precipitated amorphous non-crystalline solid organic compound, and finally separating out the fine particles of the compound.

Joshi & Bose describe, in "Studies in the Synthesis of Warfarin[3-(α-Acetonylbenzyl)-4-hydroxycoumarin], *Indian Journal of Technology*, December, 1972, Vol. 10, pgs 461–462, optimum conditions for the synthesis of warfarin using sixteen different selected basic condensing agents.

Hayward describes, in "The Prototype Compound for the Oral Anticoagulants (3,3'-Methylene bis(4-hydroxycoumarin))", *Journal of Chemical Education*, January, 1984, Vol.61, No. 1, pgs 87–88, a synthesis for producing 3,3'-Methylene bis(4-hydroxycoumarin) by dropwise addition of o-hydroxyacetophenone and diethyl carbonate in dry toluene to a stirred suspension of sodium hydride in dry toluene maintained at 110° C. This is followed by distillation removal of ethanol formed, cooling, extraction with water, and filtration. The filtrate is acidified with hydrochloric acid to precipitate the 4-hydroxycoumarin which is then filtered, washed and vacuum dried as dry as possible. The product is finally recrystallized in 50% aqueous ethanol for 90–91% yield as needle-like crystals.

Ivanov et al. describe, in "New Efficient Catalysts in the Synthesis of Warfarin and Acenocoumarol", *Arch. Pharm.*, 323, 521–522 (1990), the addition, under stirring, of water and various selected catalysts to 4-hydroxycoumarin and either of two unsaturated ketones. This is followed by reflux with stirring for any of various selected times ranging from 2 hours to 20 hours. The product is filtered, pulverized, washed with hot water, cooled, followed by washing with ether and may then be recrystallized from acetic acid or ethyl acetate.

As can be seen from the art, there is a large amount of interest in viable synthetic routes or purification steps to obtain warfarin in its varying forms. A need persists for an economical, commercially feasible route to produce or purify warfarin and related derivatives.

SUMMARY OF THE INVENTION

The present invention provides processes which are flexible, cost effective, and commercially viable methods of manufacturing or producing products from 2-hydroxyacetophenone (2-HAP). These products are economically produced in a single vessel and provide potential commercial value at each optional endpoint. An advantage of the invention is the minimized points at which contamination has the potential of being introduced. Of particular interest of the available products are 4-hydroxycoumarin, warfarin-alkali salt, preferably warfarin sodium and warfarin-alkali salt-isopropyl alcohol (2-propanol) complex, more preferably warfarin-sodium-isopropyl alcohol complex. The present invention eliminates the drying step as detailed by Hayward and avoids the need to pulverize and dry in accordance with Ivanov.

As is known, these compounds are useful as vitamin K dependent anticoagulants in the treatment of humans and animals. In different doses, they are also useful as rodenticide.

DETAILED DESCRIPTION

A process is provided for synthesizing, from 2-hydroxyacetophenone, the compounds: 4-hydroxycoumarin, optionally warfarin, optionally warfarin alkali salt, preferably warfarin-alkali metal, especially warfarin sodium, optionally warfarin-alkali salt-isopropyl alcohol complex, preferably warfarin-alkali metal-isopropyl alcohol complex, especially warfarin-sodium-isopropyl alcohol complex, and warfarin sodium isopropanol complex of less than or equal to about 100 mm particle size, comprising:

a) reacting 2-hydroxyacetophenone, organic carbonate, such as dialkyl carbonate, preferably diethyl carbonate; and effective base, including alkali alkoxide or aryloxide, particularly alkali metal alkoxide, especially sodium alkoxide, more preferably sodium methoxide or sodium ethoxide; hydride, particularly alkali metal hydride, especially sodium hydride;

b) removing hydroxyl-functionalized species formed by ester hydrolysis, which will likely be alcohol;

c) treating the result, of b), with suitable polar liquid, preferably water;

d) treating the result, of c) to place its pH within the range of about 1 to about 2, preferably with suitable acid, particularly mineral acids, especially hydrochloric acid;

e) separating the resulting precipitate and removing residual acid, preferably by washing with suitable polar liquid, particularly water, to achieve an about neutral pH, this precipitate may be dried and the resulting 4-hydroxy coumarin, and its derivatives, or combinations thereof collected for use;

or, optionally, further f) reacting the resulting precipitate of e) with effective or suitable ketone, particularly $\alpha$-$\beta$ unsaturated ketone, especially aryl substituted, preferably benzalacetone (benzylidene acetone), or combinations thereof, in a suitable protic solvent in which the product is insoluble, particularly water, and in presence of an effective phase-transfer catalyst, such as quaternary alkyl or aryl ammonium halide salt, wherein the alkyl may contain from 1 to about 10 carbon atoms;

g) treating the result of f) with solvent to extract the product, preferably organic acetate, particularly ethyl acetate;

h) removing the protic solvent, preferably aqueous, layer and concentrating the product-bearing solvent layer as needed to allow warfarin crystallization;

i) separating solid warfarin which has crystallized from extracting solvent, which may be collected and further dried for use;

or, optionally, further j) treating the result of i) with effective alkali including hydroxides, carbonates, and bicarbonates, preferably alkali metal alkoxide, especially sodium alkoxide;

k) removing other organic solvents and drying to separate warfarin alkali salt, particularly warfarin alkali metal, especially warfarin sodium, or optionally, further l) treating the result of k) with isopropyl alcohol, preferably having less than about 0.2 wt % water, more preferably anhydrous, preferably at temperatures less than about 25° C.;

and, finally m) separating warfarin-alkali salt-isopropyl alcohol complex, preferably as small crystals, preferably having more than about a majority of a size less than about 100 µm. For purity enhancement or physical adjustment of the final form, the warfarin-alkali salt-isopropyl alcohol complex, resulting from l), may optionally be treated further by n) dissolving to provide an about 40 to about 50 wt % solution in ethanol;

o) adding the warfarin-alkali salt-isopropyl alcohol complex/ethanol solution to isopropyl alcohol, preferably having less than about 0.2 wt % water, especially anhydrous, preferably maintained at less than about 25° C., especially between about 5 and less than about 25° C., such that the solution has an isopropyl alcohol :warfarin metal ratio, of greater than about 23:1 (wt/ wt), preferably such that the ethanol content of the solution is about 15 wt % or less; with agitation, and finally, p) collecting the warfarin-alkali salt-isopropyl alcohol complex as crystals, preferably as free, uniform crystals, especially as crystals having isopropyl alcohol content of about 8 to about 8.5 wt % and crystal sizes such that at least more than about a majority are less than about 100 µm in size, particularly at least about 60% are about 60 µm or less in size.

For this process, there are variations of some of the processing conditions which may provide somewhat differing results. Some of the varying results may be more preferable and include yielding chosen final products providing enhanced purity, improved stability, better flowability, preferred crystal morphology, and easier handling characteristics. Such variables include time of reactions, temperature of reactions, level of agitation, reaction vessel surface characteristics, and temperature ranges allowed during some steps, particularly formation steps. Such process variables should be explored in a sensible engineering fashion for the particular equipment available and for the particular product desired. We include such process variations as part of our invention.

To illustrate the process of our invention and its usefulness, several examples follow. These are intended only to exemplify our invention and do not define its full scope.

EXAMPLES

Example 1

Avoiding vigorous boiling or distillation, a solution of 60.5 g (0.44 mole) 2-HAP, available from Hoechst Celanese, Corpus Christi, Tex., and 118.13 g (1.1 mole) diethyl carbonate, available from Miles or SNPE Chimie, in 400 ml of dry toluene, available from George Mann & Co., was added dropwise over about 30 minutes to 26.4 g (0.66 mol) of sodium hydride, available from Morton Performance Chemicals, (60% in mineral oil) which was suspended in toluene. The NaH suspension in toluene was maintained at about 110° C.

During addition, ethanol was formed and removed by distillation. After removal of all ethanol, the thick mixture was cooled to about 20° C. and carefully treated with about a liter of water. The reaction mixture was treated with concentrated hydrochloric acid, available from Astro Chemicals, to bring the pH into the range of about 1–2. The resulting precipitate was collected by filtration, washed with about a liter of water and dried. The resulting compound was identified, according to literature standards by MS, NMR, IR spectroscopy, thin-layer chromatography, MP and other accepted methods as 4-hydroxycoumarin with a total yield of 71.3 g or 87%.

Example 2

Except as noted, amounts employed were the same as example 1. For this series of experiments, solution of 2-HAP and diethyl carbonate in 300 ml of dry toluene was added dropwise to a stirred mechanical suspension of NaH in 600 ml of toluene which was maintained at about 110° C. To maintain the temperature in the range of about 108° C. to 110° C. and to maintain the distillation of the ethanol produced, this addition occurred over about a 30 minute period. The color of the reaction mixture changed from a tin-ash color to a yellow/green color. After completion of the addition, the reaction mixture was heated for about another 30 minutes.

The reaction mixture was cooled to about 60° C. and followed by the cautious addition of about 900 ml of water while stirring. The phases were then allowed to separate followed by decanting of the toluene layer. An additional about 500 ml of toluene was added while stirring and the layers were allowed to separate. The toluene layer was again decanted off.

The aqueous layer was acidified with concentrated HCl to a pH of about 1–2, by pH paper. The precipitate was separated by filtration and washed with water to a neutral pH of about 7, again by pH paper. With a coarser precipitate, the water could be decanted off after settling.

The wet solid was returned to the reaction flask to which was added 64.2 g (0.439 mol) of benzalacetone, available from Penta, 600 ml of water, and 9.2 g of a phase transfer catalyst, benzyl triethylammonium chloride, available from R.S.A. Corp., which was followed by another 250 ml of water. The reaction mixture was stirred and heated to reflux. It was noted that the reflux occurred at about 88°–89° C.; it was assumed that some volatile materials, perhaps ethanol, toluene, or 2-HAP, were left over from the previous reaction. The condenser's cooling was stopped to remove such volatile components. When the temperature reached about 99° C., the condenser cooling was restarted, stirring of the reaction mixture continued, and the mixture was heated at reflux for about two to four hours. Samples for IR, chromatography, and other means of identification were taken at this times.

The reaction mixture was treated with 750 ml of ethyl acetate which was added cautiously while the stirring continued for until the reaction mixture cooled to below about 89° C. The layers were allowed to phase separate and the organic layer was washed with 700 ml of water and heated to about 72° C. followed by decanting off of the water. After the last wash, the organic layer was concentrated to a volume of about ⅓ of the last volume by vacuum distillation. It was then filtered through a sintered glass funnel and allowed to cool in an ice-water bath to about 5°–10° C. The deposited crystals were collected by filtration, washed with about 50 ml cold ethyl acetate and dried. The warfarin was identified by thin-layer chromatography, IR, MS, NMR spectrophotometry, and other methods according to literature standards with yields, in repeated experiments, of 47–67% based on 2-HAP.

Example 3

For this series of experiments, the procedure for Example 2 was followed again except that the 4-hydroxycoumarin, its derivatives, or combinations thereof was not isolated. The basic solution obtained after the addition of water to the 2-HAP/NaH/(EtO)$_2$CO reaction was acidified to a pH of about 7. To this neutralized mixture, benzyltriethylammonium chloride was added and reaction was allowed to proceed. The warfarin sodium was identified by thin-layer chromatography, IR, MS, NMR spectrophotometry, and other methods according to literature standards with yields, in repeated experiments, of 33–52% based on 2-HAP.

Example 4

Except as noted, amounts employed were the same as example 1. In this series of experiments, 2-HAP and dialkylcarbonate in a molar ratio of 1:3 were added to a non-polar aromatic solvent, toluene or xylene were used. In another reactor, a solution of the alkali alkoxide base or alkali hydride base, dissolved in the same solvent, was heated to between 60° C. and 100° C. The 2-HAP/alkyl carbonate solution was added slowly to this base solution.

The alcohol formed by hydrolysis of carbonate ester was liberated from the base solution as the reaction proceeded. When the addition was complete, the remaining alcohol was distilled off and the reaction mixture was allowed to cool to between about 60° C. and room temperature.

Water was slowly added until there were approximately equal volumes of aqueous and organic phases. The 4-hydroxycoumarin, or its derivative, was extracted into the aqueous phase. The organic layer was decanted and disposed of.

The aqueous phase was acidified until the coumarin, its derivatives or combinations, precipitated. The product was then filtered and washed with water. This crude wet cake was then added back to the reactor with water and benzalacetone. A phase transfer catalyst was added and the mixture was heated for about two to about four hours.

The warfarin formed was then extracted into ethyl acetate, available from Ashland Chemical. The ethyl acetate was then back extracted with water and concentrated by distillation, vacuum distillation would be functional also, to improve yield. The concentrated ethyl acetate layer was then cooled to below about 25° C. and the warfarin was filtered out. The cake was dried, suspended in ethanol and base, in the form of sodium ethoxide, available from Aldrich or Elan as 21% solution in ethanol. This solution was then treated with activated charcoal, (DARCO 2040) available from Darco, to remove color. The warfarin sodium solution was concentrated by distillation until about 80% of the ethanol had been distilled. Isopropyl alcohol, available from Houghton Chemical, was added to bring the solution back to the original volume. The solution was distilled and isopropyl alcohol was used to replace the overhead until the ethanol concentration in the solution was less than about 18%. The solution was allowed to cool and the product was filtered. A saturated solution of this wet cake in ethanol, available from McCormick, was made and added to a well agitated, anhydrous isopropyl solution maintained at less than about 25° C. The warfarin sodium-isopropyl alcohol complex was crystallized out over an about three hour period in small, uniform crystals. The product was filtered and dried in the absence of moisture.

Example 5

2-HAP (110.1 g, 0.81 mols) and Diethylcarbonate (2.2 mols) in a molar ratio of 1:3 were added to a nonpolar aromatic solvent such as toluene, or xylene. In another reactor, a solution of the sodium alkoxide base or sodium hydride base (1.3 mols), dissolved in the same solvent, was heated to between 60° C. and 100° C. The 2-HAP/ diethylcarbonate solution was added slowly to this base solution. The alcohol was liberated from the base solution as the reaction proceeded. When the addition was complete, the remaining alcohol was distilled off and the reaction was allowed to cool to between 60° C. and room temperature. Water was slowly added until there were approximately equal volumes of water to organic phase. The 4-hydroxy coumarin derivative was extracted into the water phase, and the organic layer was decanted. The aqueous phase was acidified to pH of 2–4 until the 4-hydroxy coumarin precipitated. The product was then filtered and washed with water (805 g). This crude wet cake was then added back to the reactor with water (969 g) and benzalacetone (142 g). A phase transfer catalyst such benzyltriethylammonium halide or quat-ammonium salt (0.12 mols) was added and the solution was heated for 2–4 hours. The warfarin was extracted into ethylacetate (1292 g, 14.7 mols). The ethyl acetate was back extracted with water (646 g, 35.9 mols) then concentrated by distillation. The ethylacetate layer was then cooled to <25° C. and the warfarin was filtered. This cake was then treated with an ethanol (717–847 g) and sodium ethoxide solution (1 molar equivalent to Warfarin) until it dissolved. This solution was treated with activated carbon (5–20 g). This warfarin sodium solution was concentrated by distillation until 80% of the ethanol had been distilled. Isopropanol was added to bring the solution back to the original volume. The solution was distilled and isopropanol was used to replace the overhead until the ethanol concentration in the solution was less than 18%. The solution was allowed to cool and the product was filtered. A saturated solution of this wet cake in ethanol (40–50 wt % Warfarin Na IPA Complex in ethanol) was made and added to a well agitated, anhydrous isopropanol solution (IPA: Warfarin Sodium Isopropanol, wt to wt 17–20:1) kept at less than 25° C. The warfarin IPA complex was crystallized out over a 4 hour period in small uniform crystals. The product was filtered and dried in the absence of moisture.

Example 6

2-HAP (110.1 g, 0.81 mols) and diethylcarbonate (2.2 mols) in a molar ratio of 1:3 were added to a nonpolar aromatic solvent such as toluene, or xylene. In another reactor, a solution of the alkalai alkoxide base or alkali hydride base (1.3 mols), dissolved in the same solvent, was heated to between 60° C. and 100° C. The 2 HAP/alkyl carbonate solution was added slowly to this base solution. The alcohol was liberated from the base solution as the reaction proceeded. When the addition was complete, the remaining alcohol was distilled off and the reaction was allowed to cool to between 60° C. and room temperature. Water was slowly added until there were approximately equal volumes of water to organic phase. The 4-hydroxy coumarin derivative was extracted into the water phase and the organic layer was decanted. The aqueous phase was acidified to pH of 2–4 until the coumarin or derivative precipitated. The product was then filtered and washed with water (805 g). This crude wet cake was then added back to the reactor with water (969 g) and benalacetone (142 g). A phase transfer catalyst such as benzyltriethylammonium halide or quat-ammonium salt (0.12 mols) was added and the solution was heated for 2–4 hours. The warfarin was extracted into ethylacetate (1292 g). The ethyl acetate was back extracted with water (646 g) then concentrated by distillation. The ethylacetate layer was then cooled to <25° C. and the warfarin was filtered. This cake was then treated with an ethanol (717–847 g) and sodium ethoxide (1 molar equivalent to Warfarin) solution it dissolved. This solution was treated with activated carbon (5 to 20 g). This saturated solution of warfarin sodium in ethanol (40–50 wt % Warfarin Na IPA Complex in ethanol) was added to a well agitated, anhydrous isopropanol solution kept at less than 25° C. The warfarin IPA complex was crystallized over a 4 hour period to yield small uniform crystals. The product was filtered and dried in the absence of moisture.

Example 7

Except as noted, amounts employed were the same as example 1. For this series of experiments, 2-HAP and dialkylcarbonate in a molar ratio of 1:3 were added to a non-polar aromatic solvent, toluene or xylene may be used. In another reactor, a solution of the alkali alkoxide base or alkali hydride base, dissolved in the same solvent, was heated to between 60° C. and 100° C.

The 2-HAP/alkyl carbonate solution was added slowly to this base solution. The alcohol formed by carbonate ester hydrolysis was liberated from the base solution as the reaction proceeded. When the addition was complete, the remaining alcohol was distilled off and the reaction mixture was allowed to cool to between about 60° C. and room temperature.

Water was slowly added until there were approximately equal volumes of aqueous and organic phases. The 4-hydroxycoumarin derivative was extracted into the aqueous phase. The organic layer was decanted and disposed of. The aqueous phase was acidified until the coumarin, its derivatives, or combinations, precipitated. The product was then filtered and washed with water.

This crude wet cake was then added back to the reactor with water and benzalacetone. A phase transfer catalyst was added and the mixture was heated for about two to about four hours. The warfarin was then extracted into ether. The ether was then back extracted with water and concentrated by distillation to improve yield. The ether layer was then cooled to below about 25° C. and the warfarin was filtered out. This cake was then treated with methanol and sodium methoxide solution until it dissolved. This solution was treated with activated charcoal to remove color. This saturated solution of warfarin sodium in methanol was added to well agitated, anhydrous isopropyl alcohol (IPA) and maintained below about 25° C. The warfarin-IPA complex was crystallized out over an about three hour period to yield small, uniform crystals. The product was filtered and dried in the absence of moisture.

As may be easily seen from these examples, our synthesis approach is flexible and economically attractive, particularly when run in a single reaction vessel without intermediate isolation of compounds, cleaning, and transfers of material. Those of skill in the art will recognize modifications of our synthetic route which are not specifically described here but which will yield expected improvements through good engineering and process optimization. We consider such modifications as facets and aspects of our invention which we claim.

We claim:

1. Process of synthesizing, from 2-hydroxyacetophenone, the compound warfarin, comprising:
   a) reacting 2-hydroxyacetophenone, carbonate ester, and effective base;
   b) removing hydroxyl-functionalized species formed by ester hydrolysis;
   c) treating the result of b) with a suitable polar liquid,
   d) treating the result of c) to place its pH within the range of about 1 to about 2;

e) separating the resulting precipitate and removing residual acid from the precipitate to achieve an about neutral pH;

f) reacting the precipitate of e) with effective unsaturated ketone, in protic solvent in which product is insoluble, and in presence of effective phase-transfer catalyst;

g) treating the result of f) with solvent to extract the product; and h) removing the protic solvent layer and concentrating the product-bearing solvent layer as needed to allow warfarin crystallization.

2. Process of synthesizing, from 2-hydroxyacetophenone, the compound warfarin alkali salt, comprising:

a) reacting 2-hydroxyacetophenone, carbonate ester, and effective base;

b) removing hydroxyl-functionalized species formed by ester hydrolysis;

c) treating the result orb) with a suitable polar liquid, d) treating the result of c) to place its pH within the range of about 1 to about 2;

e) separating the resulting precipitate and removing residual acid from the precipitate to achieve an about neutral pH;

f) reacting the precipitate of e) with effective unsaturated ketone, in a protic solvent in which warfarin product is insoluble, and in presence of effective phase-transfer catalyst;

g) treating the result of f) with solvent to extract the warfarin product;

h) removing the protic solvent layer and concentrating the warfarin-bearing solvent layer as needed to allow warfarin crystallization;

i) separating solid warfarin;

j) treating the result of i) with effective alkali, alkoxide, hydroxide, or combinations;

k) removing other organic solvents and drying to separate warfarin alkali salt.

3. Process of synthesizing, from 2-hydroxyacetophenone, the compound warfarin-alkali salt-isopropyl alcohol complex, comprising:

a) reacting 2-hydroxyacetophenone, carbonate ester, and effective base;

b) removing hydroxyl-functionalized species formed by ester hydrolysis;

c) treating the result of b) with a suitable polar liquid, d) treating the result of c) to place its pH within the range of about 1 to about 2;

e) separating the resulting precipitate and removing residual acid from the precipitate to achieve an about neutral pH;

f) reacting the precipitate of e) with effective unsaturated ketone, in protic solvent in which warfarin product is insoluble, and in presence of effective phase-transfer catalyst;

g) treating the result of f) with solvent to extract the warfarin product;

h) removing the protic solvent layer and concentrating the warfarin product-bearing solvent layer as needed to allow warfarin crystallization;

i) separating solid warfarin;

j) treating the result of i) with effective alkali, alkoxide, hydroxide, or combinations;

k) removing other organic solvents and drying to separate warfarin alkali salt;

l) treating the result of k) with isopropyl alcohol; and m) separating warfarin-alkali salt-isopropyl alcohol complex.

4. Process of claim 1 wherein a) carbonate ester is dialkyl carbonate, and effective basic reagent is alkoxide, aryloxide, hydroxide, hydride, or combinations thereof;

b) hydroxyl-functionalized species formed is alkyl alcohol;

c) suitable polar liquid is water;

d) treating is accomplished with suitable acid;

e) removing residual acid is accomplished by washing with suitable polar liquid; and, f) effective unsaturated ketone is $\alpha$-$\beta$-unsaturated ketone, suitable protic solvent in which product is insoluble is water, and effective phase-transfer catalyst is amine, quaternary ammonium halide salt, or combinations thereof;

g) solvent to extract is organic acetate;

h) protic solvent layer is aqueous; and, i) solid warfarin is separated by decanting, filtration, centrifugation, settling, or combinations thereof.

5. Process of claim 4 wherein a) dialkyl carbonate is diethyl carbonate and alkoxide, aryloxide, hydroxide, hydride, or combinations thereof is sodium methoxide or ethoxide, sodium hydroxide, sodium hydride, or combinations b) alkyl alcohol is ethanol;

c) suitable polar liquid is water;

d) suitable acid is mineral acid;

e) suitable polar liquid is water;

f) $\alpha$-$\beta$-unsaturated ketone has aromatic substituent;

g) organic acetate is alkyl acetate;

h) protic solvent layer is aqueous; and, i) solid warfarin is separated by decanting, filtration, centrifugation, settling, or combinations thereof.

6. Process of claim 5 wherein a) alkoxide, aryloxide, hydroxide, hydride, or combinations thereof is sodium ethoxide, sodium hydride, or combinations thereof;

b) alkyl alcohol is ethanol;

c) suitable polar liquid is water;

d) mineral acid is hydrochloric acid;

e) suitable polar liquid is water;

f) $\alpha$-$\beta$-unsaturated ketone is benzalacetone;

g) alkyl acetate is ethyl acetate;

h) protic solvent layer is aqueous;

i) solid warfarin is separated by decanting, filtration, centrifugation, settling, or combinations thereof.

7. Process of claim 2 wherein a) carbonate ester is dialkyl carbonate, and effective basic reagent is alkoxide, aryloxide, hydroxide, hydride, or combinations thereof;

b) hydroxyl-functionalized species formed is alkyl alcohol;

c) suitable polar liquid is water;

d) treating is accomplished with suitable acid;

e) removing residual acid is accomplished by washing with suitable polar liquid;

f) effective unsaturated ketone is $\alpha$-$\beta$-unsaturated ketone, suitable protic solvent in which product is insoluble is water, and effective phase-transfer catalyst is amine, quaternary ammonium halide salt, or combinations thereof
g) solvent to extract is organic acetate;
h) protic solvent layer is aqueous;
i) solid warfarin is separated by decanting, filtration, centrifugation, settling, or combinations thereof
j) effective alkali, alkoxide, hydroxide, or combinations thereof is selected from sodium or potassium hydroxide or carbonate, sodium or potassium methoxide or ethoxide, or combinations thereof; and,
k) warfarin alkali salt is warfarin sodium or potassium.

8. Process of claim 7 wherein
a) dialkyl carbonate is diethyl carbonate and alkoxide, aryloxide, hydroxide, hydride, or combinations thereof is sodium methoxide or ethoxide, sodium hydroxide, sodium hydride, or combinations;
b) alkyl alcohol is ethanol;
c) suitable polar liquid is water;
d) suitable acid is mineral acid;
e) suitable polar liquid is water;
f) α-β-unsaturated ketone has aromatic substituent;
g) organic acetate is alkyl acetate;
h) protic solvent layer is aqueous;
i) solid warfarin is separated by decanting, filtration, centrifugation, settling, or combinations thereof
j) effective alkali, alkoxide, hydroxide, or combinations thereof is selected from sodium hydroxide, sodium ethoxide, or combinations thereof; and,
k) warfarin alkali salt is warfarin sodium.

9. Process of claim 8 wherein
a) alkoxide, aryloxide, hydroxide, hydride, or combinations thereof is sodium ethoxide, sodium hydride, or combinations thereof;
b) alkyl alcohol is ethanol;
c) suitable polar liquid is water;
d) mineral acid is hydrochloric acid;
e) suitable polar liquid is water;
f) α-β-unsaturated ketone is benzalacetone;
g) alkyl acetate is ethyl acetate;
h) protic solvent layer is aqueous;
i) solid warfarin is separated by decanting, filtration, centrifugation, settling, or combinations thereof;
j) effective alkali, alkoxide, hydroxide, or combinations thereof is sodium ethoxide;
k) warfarin alkali salt is warfarin sodium.

10. Process of claim 3 wherein
a) carbonate ester is dialkyl carbonate, and effective basic reagent is alkoxide, aryloxide, hydroxide, hydride, or combinations thereof;
b) hydroxyl-functionalized species formed is alkyl alcohol;
c) suitable polar liquid is water;
d) treating is accomplished with suitable acid;
e) removing residual acid is accomplished by washing with suitable polar liquid;
f) effective unsaturated ketone is α-β-unsaturated ketone, suitable protic solvent in which product is insoluble is water, and effective phase-transfer catalyst is amine, quaternary ammonium halide salt, or combinations thereof;
g) solvent to extract is organic acetate;
h) protic solvent layer is aqueous;
i) solid warfarin is separated by decanting, filtration, centrifugation, settling, or combinations thereof
j) effective alkali, alkoxide, hydroxide, or combinations thereof is selected from sodium or potassium hydroxide or carbonate, sodium or potassium methoxide or ethoxide, or combinations thereof;
k) warfarin alkali salt is warfarin sodium or potassium;
l) isopropyl alcohol has less than 0.2 wt % water in solution; and
m) warfarin-alkali salt-isopropyl alcohol complex is separated as crystals.

11. Process of claim 10 wherein
a) dialkyl carbonate is diethyl carbonate and alkoxide, aryloxide, hydroxide, hydride, or combinations thereof is sodium methoxide or ethoxide, sodium hydroxide, sodium hydride, or combinations;
b) alkyl alcohol is ethanol;
c) suitable polar liquid is water;
d) suitable acid is mineral acid;
e) suitable polar liquid is water;
f) α-β-unsaturated ketone has aromatic substituent;
g) organic acetate is alkyl acetate;
h) protic solvent layer is aqueous;
i) solid warfarin is separated by decanting, filtration, centrifugation, settling, or combinations thereof;
j) effective alkali, alkoxide, hydroxide, or combinations thereof is selected from sodium hydroxide, sodium ethoxide, or combinations thereof;
k) warfarin alkali salt is warfarin sodium
l) isopropyl alcohol having less than 0.2 wt % water; and
m) warfarin-sodium-isopropyl alcohol complex is separated as crystals.

12. Process of claim 11 wherein
a) alkoxide, aryloxide, hydroxide, hydride, or combinations thereof is sodium ethoxide, sodium hydride, or combinations thereof;
b) alkyl alcohol is ethanol;
c) suitable polar liquid is water;
d) mineral acid is hydrochloric acid;
e) suitable polar liquid is water;
f) α-β-unsaturated ketone is benzalacetone;
g) alkyl acetate is ethyl acetate;
h) protic solvent layer is aqueous;
i) solid warfarin is separated by decanting, filtration, centrifugation, settling, or combinations thereof
j) effective alkali, alkoxide, hydroxide, or combinations thereof is sodium ethoxide;
k) warfarin alkali salt is warfarin sodium;
l) isopropyl alcohol is anhydrous; and
m) warfarin-sodium-isopropyl alcohol complex is warfarin-sodium-isopropyl alcohol complex and is separated as crystals with at least about a majority of them being less than or equal to about 100 μm in size.

13. Process of claim 1 accomplished in a single vessel or reactor.

14. Process of claim 2 accomplished in a single vessel or reactor.

15. Process of claim 11 wherein result of m) is subjected to further treatment, comprising:

n) dissolving warfarin alcohol complex to provide an about 40 to about 50 wt % solution in ethanol;

o) adding the result of n) to isopropyl alcohol, such that the resulting solution has an isopropyl alcohol:warfarin metal ratio, in 1:kg, greater than at least about 23:1; and finally, p) collecting the warfarin-alkali salt-isopropyl alcohol complex as fine, uniform crystals having isopropyl alcohol content of about 8 to about 8.5 wt %.

16. Process of claim 12 wherein result of m) is subjected to further treatment, comprising:

n) dissolving warfarin alcohol complex to provide an about 40 to about 50 wt % solution in ethanol;

o) adding the result of n) to isopropyl alcohol, such that the resulting solution has an isopropyl alcohol:warfarin metal ratio, in 1:kg, greater than at least about 23:1; and finally, p) collecting the warfarin-alkali salt-isopropyl alcohol complex as fine, uniform crystals having isopropyl alcohol content of about 8 to about 8.5 wt %.

17. Process of claim 15 accomplished in a single vessel or reactor.

18. Process of claim 16 accomplished in a single vessel or reactor.

* * * * *